United States Patent [19]

Ten Hoeve et al.

[11] Patent Number: 5,463,050
[45] Date of Patent: Oct. 31, 1995

[54] METHOD OF PREPARING ARYL(HOMO)PIPERAZINES

[75] Inventors: Wolter Ten Hoeve; Jantje R. G. Thiecke; Hans Wynberg; Chris G. Kruse, all of Weesp, Netherlands

[73] Assignee: Duphar International Research, B.V., Weesp, Netherlands

[21] Appl. No.: 17,497

[22] Filed: Feb. 12, 1993

[30] Foreign Application Priority Data

Feb. 18, 1992 [EP] European Pat. Off. .............. 92200468

[51] Int. Cl.$^6$ ...................... C07D 295/08; C07D 243/08
[52] U.S. Cl. ...................... 540/575; 544/358; 544/359; 544/360
[58] Field of Search ............................ 540/575; 544/358, 544/359, 360

[56] References Cited

U.S. PATENT DOCUMENTS

| | | | |
|---|---|---|---|
| 3,173,917 | 3/1965 | Starker et al. . | |
| 4,831,031 | 5/1989 | Love | 514/254 |
| 5,086,056 | 2/1992 | Janssens et al. | 540/575 |
| 5,110,928 | 5/1992 | Schroeder et al. . | |

FOREIGN PATENT DOCUMENTS

| | | |
|---|---|---|
| 0556889 | 9/1993 | European Pat. Off. . |
| 947606 | 1/1964 | United Kingdom . |

OTHER PUBLICATIONS

*J. Heterocyclic Chemistry*, vol. 14, No. 3, May 1977, pp. 535–536 Bissell, "A Novel Synthesis of 1,4–Diarylpiperazines".

*Jounral of Medicinal Chemistry*, vol. 8, No. 1, Jan. 1965, R. Ratouis et al., "Synthesis and Pharmacological Study of New Piperazine Derivatives".

*Primary Examiner*—Nicholas Rizzo
*Attorney, Agent, or Firm*—Stevens, Davis, Miller & Mosher

[57] ABSTRACT

The present invention is concerned with a method for the preparation of a compound of the general formula 2

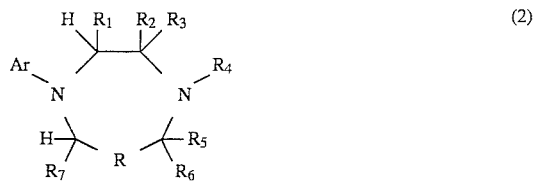

by reaction of a compound of the formula 3

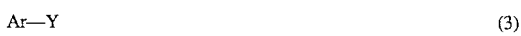

with a compound of the general formula 4

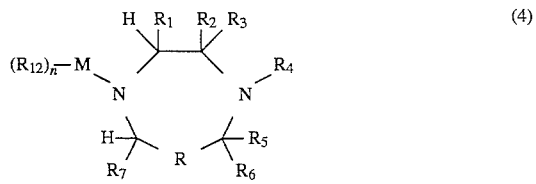

wherein

Ar means a (hetero)aryl group, preferably selected from phenyl, naphtyl, furyl, thienyl, pyridyl, bicylic heteroaryl and tricyclic heteroaryl, which (hetero)aryl group is optionally sustituted with one to five non-strongly-electron-withdrawing substituents;

M is a metal from the groups I or II of the periodic table;

$R_{12}$ is an electronegative group; and is 0 or 1.

The invention also relates to compounds prepared according to this method and to new substituted aryl(homo)piperazines.

6 Claims, No Drawings

METHOD OF PREPARING ARYL(HOMO)PIPERAZINES

The present invention is concerned with a method for the preparation of aryl(homo)piperazine derivatives.

Among arylpiperazine derivatives many have useful pharmaceutical properties, in particular due to their influence on the serotonergic transmission within the Central Nervous System. Several of these derivatives already have found their way to the market, such as urapidil, trazodone, buspirone, dropropizine, oxypertine and fluanisone. Furthermore, arylpiperazines having antibiotic activity are norfloxacin, difloxacin and ciprofloxacin. Many other arylpiperazine derivatives currently are under investigation.

According to one method known in the art, aryl(homo)piperazines can be prepared by a nucleophilic substitution reaction, in which an aryl precursor substituted with a nucleofugal group, such as halide, reacts with a piperazine derivative. In order for the reaction to proceed the aryl group additionally has to be provided with at least one strongly electron withdrawing group such as a cyano or a nitro group. Moreover, in many cases this electron withdrawing group should be removed afterwards, thus necessitating additional reaction steps [Schmutz & Künzle, Helvetica Chimica Acta 39, 1144–1156; 1956].

According to another method arylpiperazines can be prepared by reacting an arylamine with an electrophilic compound of the formula 1

wherein the groups X belong to the class of the well-known leaving groups, such as halide and sulphonate [Martin et al., J. Med. Chem. 32, 1052–1056; 1989], and wherein A means hydrogen or substituted (with a suitable substituent for derivatizing purposes) alkyl. However, these latter bifunctional reagents are generally very toxic and often even tumorogenic and carcinogenic on the basis of their cross-linking ability. This makes this reaction very unattractive for large scale production. Another restriction is the low nucleophilic reactivity of the arylamine nitrogen centre, especially when no electron releasing substituents are present in the aryl group. Usually, high temperatures are necessary and the yields are only moderate. Furthermore, experiments reported by Barnett & Smirz [J. Org. Chem. 41, 710–711; 1976] indicate that this method will not be suitable for the preparation of arylpiperazines which are regioselectively substituted in the piperazine ring by e.g. alkyl groups.

According to again another method, described in U.S. Pat. No. 3,173,917, substituted phenylpiperazines can be prepared by reacting piperazine or substituted piperazine and a haloaryl compound with a bimolar quantity of an aryllithium compound. It will de obvious, that such an excess of expensive lithium compound will make the production process not attractive from an economical point of view.

The disadvantages of the prior art methods are overcome by the method according to the present invention. This method for the preparation of a compound of the general formula 2

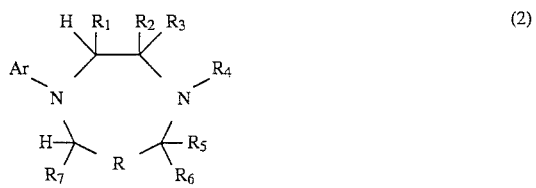

is characterized in that a compound of the formula 3

is reacted with a compound of the general formula 4

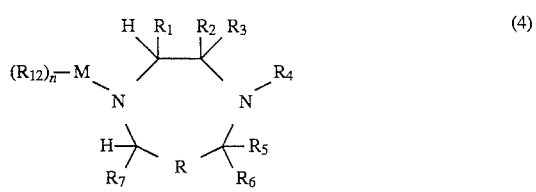

wherein

Ar means a (hetero)aryl group, preferably selected from phenyl, naphthyl, furyl, thienyl, pyridyl, bicylic heteroaryl and tricyclic heteroaryl, which (hetero)aryl is optionally subtituted with one to five non-group strongly-electron-withdrawing substituents;

M means a metal from the groups I or II of the periodic table;

$R_{12}$ is an electronegative group selected from halogen, lower alkoxy, lower alkanoyloxy and a group of the general formula 9;

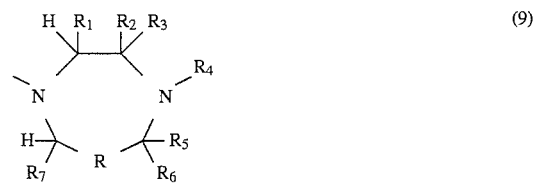

n is, dependent on the valence of M, 0 or 1;

R may be absent and represent a bond linking the two adjacent carbon atoms or means a group —$CR_8R_9$— or carbonyl; $R_1$–$R_3$ and $R_5$–$R_9$ independently of each other mean hydrogen, optionally substituted lower alkyl, or optionally substituted phenyl(lower)alkyl;

$R_4$ means hydrogen or a lower alkyl, aryl, aryl(lower)alkyl, lower alkylsulphonyl, arylsulphonyl, lower trialkylsilyl, triarylsilyl, lower alkylcarbonyl, arylcarbonyl, lower alkyloxycarbonyl, or aryloxycarbonyl group; and Y means $OR_{10}$ [wherein $R_{10}$ means lower alkyl or alkyloxyalkyl, optionally substituted phenyl or optionally substituted phenyl(lower)alkyl], chlorine, fluorine, or $SO_2R_{11}$, wherein $R_{11}$ means hydroxy, OM (wherein M has the above meaning), lower alkyl, di(lower)alkylamino, wherein the alkyl groups together with the amino-N may form an optionally (lower)alkyl-substituted heterocyclic ring which may comprise a second heteroatom selected from N, O and S, diarylamino or phenyl.

Lower alkyl means $C_1$–$C_{10}$ straight or branched alkyl as well as $C_3$–$C_8$ cycloalkyl.

Suitable non-strongly-electron-withdrawing groups for the symbol Ar are, for example, deuterium, tritium, lower alkyl, alkenyl, alkoxy and alkylthio, phenylthio, hydroxy, halogen, trihalomethyl, di(lower)alkylamino, wherein the alkyl groups together with the amino-N may form an optionally (lower)alkyl-substituted heterocyclic ring which may comprise a second heteroatom selected from N, O and S, diphenylamino, optionally substituted phenyl, phenoxy and phenyl(lower)alkoxy, $(C_1-C_2)$alkylenedioxy, and $SO_2R_{11}$, wherein $R_{11}$ has the above meaning.

Halogen means fluorine, chlorine, bromine or iodine.

Suitable examples of (hetero)aryl groups are defined above; phenyl and naphthyl are examples of aryl groups, furyl, thienyl and pyridyl of heteroaryl groups. Suitable examples of bicyclic and tricyclic heteroaryl groups are benzo-annelated and dibenzo-annelated heteroaryls, as defined above.

The alkyl group in the meanings of $R_1-R_9$ may be substituted with halogen, lower alkoxy, hydroxy or protected hydroxy. The phenyl group may be substituted, as mentioned above, e.g. with halogen, with lower alkyl, alkoxy, alkylthio or haloalkyl, with hydroxy or with di(lower)alkylamino.

The compound of formula 4 can be prepared from the compound of formula 5

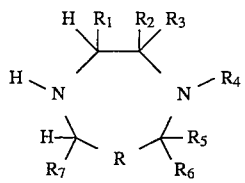
(5)

by methods known in the art, e.g. by a reaction with a strongly basic organic or inorganic metallic reagent containing M, such as metallic hydrides, amides, aryls, alkyls and alkenyls or with the metal M as such. Suitable examples of metal M are lithium, sodium and magnesium; lithium is the preferred metal.

The reaction according to the present invention proceeds at a temperature between room temperature and the reflux temperature of the solvent. The solvent should be neutral and inert with respect to the metalic reactant, except in case the substrate Ar—Y is used as the solvent. Suitable solvents are cyclic ethers (such as tetrahydrofuran, dioxan), acyclic ethers (such as methyl-t-butyl ether), cyclic and acyclic tertiary amines [such as triethylene diamine (DABCO), N,N'-dimethylpiperazine, N,N,N',N'-tetramethyl-ethylenediamine and N,N,N',N'',N''-pentamethyldiethylenetriamine], and hydrocarbons (such as toluene, styrene or Ar—Y), or mixtures thereof.

The method according to the present invention is not only appropriate for the introduction of unsubstituted (homo)piperazines but can also be used for the regiospecific synthesis of compounds wherein at least one of R and substituents $R_1-R_3$ and $R_5-R_7$ is not hydrogen in the (homo)piperazine ring of compound 5.

The reaction according to the present invention is surprising in that the nucleophilic substitution takes place in the absence of strong electron-withdrawing substituents at the aromatic group (Ar). It was demonstrated that the reaction does not or only to a minor extent proceed via the benzyn mechanism, which by analogy with the observed reaction of strong bases (such as n-butyllithium) with compounds of the type Ar-halide or Ar—$OCH_3$ [Katsoulos et al., Synlett 1990, 731–732] could also be expected for reactions of the present type. Indeed it was observed, that under the applied reaction conditions, compounds of the type Ar—Br and Ar—I reacted apparently via this benzyn mechanism, leading to mixtures of regio-isomeric products, where the (homo)piperazine group was also introduced into the aromatic ring at a different position than the position previously occupied by the Br or I substituent. This phenomenon can also be observed in the method of preparing substituted phenylpiperazines, as described in the before-mentioned U.S. Pat. No. 3,173,917. The regiospecific substitution reaction is apparently disturbed by using bromo-substituted aryl compounds as starting material.

The method of the present invention is also surprising in view of the cleavage reactions of aryl ethers with di-alkyl substituted lithium amides, leading to the formation of N,N-dialkyl-arylamines as by-products in addition to the expected phenols [described by Cuvigny et al. in J. Organometallic Chemistry 55, 41–55; 1973]. In this latter publication it is described that the substitution reaction proceeds only in the presence of the strongly polar and mutagenic solvent hexamethylphosphotriamide (HMPT) (and not e.g. in ethers), whereas the reaction of the present invention proceeds under mild conditions in apolar solvents. Furthermore, the preparation of compounds having higher alkyl groups than methyl proved difficult because of the predominant accompanying formation of the corresponding methyl compounds, due to nucleophilic displacement reactions of the di-alkyl substituted lithium amide with the solvent HMPT. Moreover, this publication teaches also the need for a considerable excess of the di-alkyl-substituted lithium amide over the aryl ether.

Hence, the advantages of the method according to the present invention over the prior art methods reside in the absence of toxic reagents, in the use of inexpensive starting compounds, in mild reaction conditions, and in the possibility to regio-selectively produce compounds, wherein at least one of the substituents $R_1-R_3$ and $R_5-R_7$ differs from hydrogen.

The present invention also relates to the compounds of the general formula 2, prepared according to the above method.

The present invention is particularly suitable for the production of aryl (homo) piperazine compounds, having a non-strongly-electron-withdrawing substituent in the aryl group, and wherein R is methylene or/and one of the substituents on the piperazine ring is methyl, because such compounds are not readily accessible up to the present.

Therefore the present invention finally relates to new aryl(homo)piperazine compounds having the general formula 7

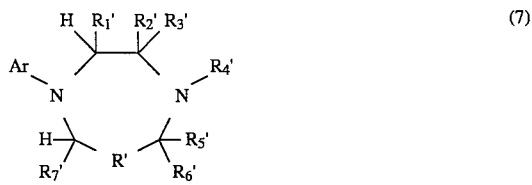
(7)

wherein

Ar has the meaning given hereinbefore;

R' may be absent and represent a bond linking the two adjacent carbon atoms, or means a methylene group;

$R_4'$ is a hydrogen atom, a lower alkyl group or an optionally substituted phenyl (lower) alkyl group; and $R_1'-R_3'$ and $R_5'-R_7'$ are hydrogen atoms or methyl groups; with the proviso, that at least one of $R_1'-R_3'$ and $R_5'-R_7'$ represents methyl, if R' is absent and represents a bond linking the two adjacent carbon atoms.

Suitable examples of these new aryl (homo) piperazine compounds can be represented by the general formula 8

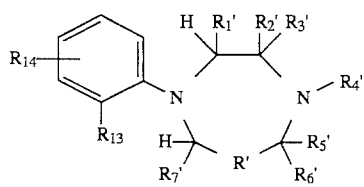

wherein

R' and $R_1'$-$R_7'$ have the meanings given hereinbefore;

$R_{13}$ is a lower alkoxy group, an optionally substituted phenyl(lower)alkoxy group or a N,N-di(lower)alkylamino group, wherein the alkyl groups together with the amino-N may constitute a heterocyclic ring, which ring may comprise an additional heteroatom selected from N, O and S; and $R_{14}$ is hydrogen or has any of the meanings of $R_{13}$;

or wherein $R_{13}$ and $R_{14}$ together constitute a $(C_1–C_2)$-alkylenedioxy group.

The invention is hereinafter illustrated by the following working examples.

EXAMPLE 1

Synthesis of
1-(2-methoxyphenyl)-4-methylpiperazine

The captioned product is synthesized according to reaction scheme 1.

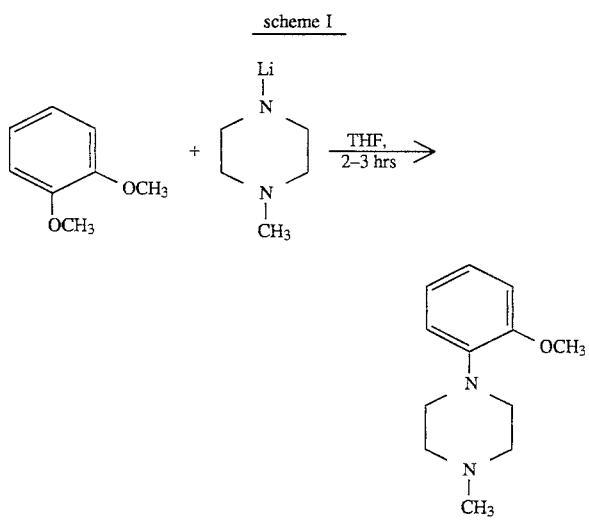

scheme I

In a dry equipment 4.4 ml (40 mmole) of N-methylpiperazine and 40 ml of THF are mixed under a nitrogen atmosphere. At a temperature of between 0° and 10° C. 18 ml of a 2.5 mol/l solution of n-butyllithium in n-hexane is added dropwise to the methylpiperazine solution. This reaction mixture is stirred for 30 minutes at 0° C. and thereafter during 1 hour at room temperature. Subsequently, 5.2 ml (40 mmole) of 1,2-dimethoxybenzene is added and the resulting mixture is heated to reflux. After 2 hours the mixture is cooled to room temperature, and thereafter it is poured into 100 ml of a diluted aqueous solution of HCl.

The resulting mixture is extracted thrice with 100 ml of toluene. The aqueous layer is titrated with NaOH to a basic pH and a white precipitate results. Then the aqueous solution is extracted once again thrice with 100 ml of toluene. The collected toluene layers are dried over $Na_2SO_4$, and the toluene is removed by evaporation giving 1-(2-methoxyphenyl)- 4-methyl-piperazine (yield 75%).

EXAMPLE 2

Analogous to the method used in Example 1 reactions of the piperazine compound of formula 6

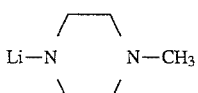

with other aryl derivatives were carried out, as shown in reaction scheme II. The piperazine substituent is regio-selectively introduced in the position marked with an asterisk. In case the substrate is provided with a single substituent, the regio-selective substitution can conveniently be demonstrated by using deuterated substrate ArY. The results are recorded in Table A below. The yields refer to isolated products.

scheme II

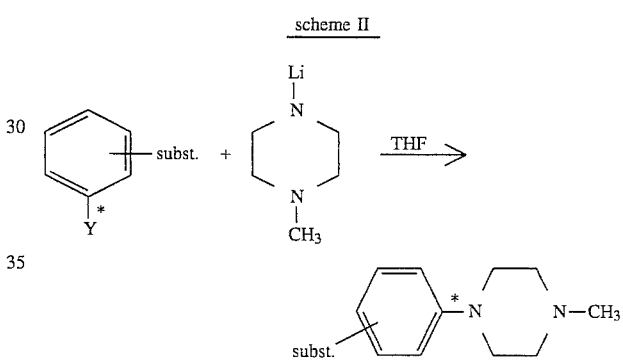

TABLE A

| Y | subst. | yield (%) |
|---|---|---|
| F | 2-OCH$_3$ | 91 |
| OCH$_3$ | — | 44 |
| OCH$_3$ | 2-OtBu | 15 |
| F | 3-OCH$_3$ | 60 |
| F | — | 85 |
| OCH$_3$ | 2,3-(OCH$_3$)$_2$ | 70 |
| OCH$_3$ | 3,5-(OCH$_3$)$_2$ | 32 |
| OC$_6$H$_5$ | — | 70 |
| OCH$_2$C$_6$H$_5$ | 2-OCH$_3$ | 65 |
| OCH$_2$C$_6$H$_5$ | 2-OCH$_2$C$_6$H$_5$, 3-OCH$_3$ | 29 |
| OCH$_3$ | 2,3-(OCH$_2$C$_6$H$_5$)$_2$ | 33 |
| OCH$_3$ | 2-OCH$_2$C$_6$H$_5$, 3-OCH$_3$ | 60 |
| F | 4-CH$_3$ | |
| F | 3-CH$_3$ | |
| F | 2,3-(OCH$_2$CH$_2$O) | 15 |
| OCH$_3$ | N⌒N—CH$_3$ (piperazinyl) | 25 |
| OC$_6$H$_4$(2-OCH$_3$) | 2-OCH$_3$ | 90 |
| OC$_6$H$_5$ | 4-OCH$_3$ | 70 |
| OCH$_3$ | 2-N(CH$_3$)$_2$ | 50 |
| SO$_3$Li | — | 75 |
| SO$_2$C$_6$H$_5$ | — | 90 |
| SO$_3$Li | 4-CH$_3$ | 16 |
| SO$_2$CH$_3$ | — | 10 |

TABLE A-continued

| Y | subst. | yield (%) |
|---|---|---|
| OCH$_2$C$_6$H$_5$ | — | 63 |
| OCH$_3$ | 4-D | 42 |
| SO$_3$H | — | 75 |
| OCH$_3$ | 3-OCH$_3$ | 75 |
| OCH$_2$C$_6$H$_5$ | 2,3-(OCH$_2$C$_6$H$_5$)$_2$ | 60 |
| OC$_6$H$_5$ | — | 70 |

EXAMPLE 3

Analogous reactions are carried out between the piperazine compound of the above formula 6 and various aryl derivatives ArY, according to reaction scheme III. The results are presented in Table B below.

Scheme III

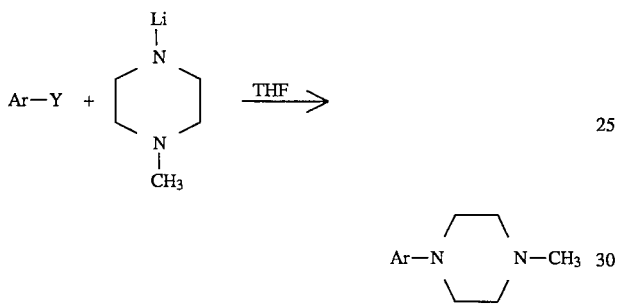

TABLE B

| Ar | Y | yield (%) |
|---|---|---|
| 1-naphthyl | OCH$_3$ | 69 |
| 2-naphthyl | OCH$_3$ | 68 |
| 2-thienyl | OCH$_3$ | 22 |
| 2-pyridyl | OCH$_3$ | 86 |
| 2-pyridyl | F | 96 |

EXAMPLE 4

Analogous reactions are also carried out between other piperazine derivatives and the aryl derivatives as shown in reaction scheme IV. The piperazine substituent is regioselectively introduced in the position marked with an asterisk. The yields are given as percentages of isolated material or of converted starting material (with **): Table C.

scheme IV

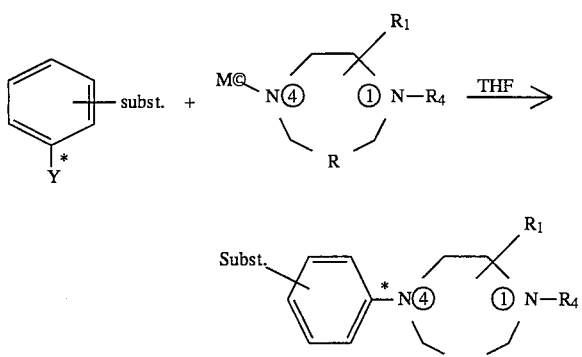

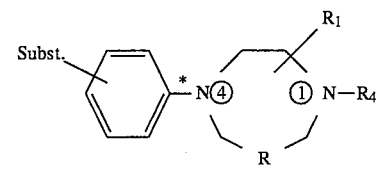

TABLE C

| Y | subst. | R$_4$ | R$_1$ | R | M' | yield (%) |
|---|---|---|---|---|---|---|
| F | 2-OCH$_3$ | CH$_3$ | H | bond | MgBr | ca. 90** |
| OCH$_3$ | 2-OCH$_3$ | CH$_3$ | H | bond | Na | 46 |
| F | 2-OCH$_3$ | CH$_3$ | H | bond | Na | ca. 90** |
| OCH$_3$ | 2,3-(OCH$_3$)$_2$ | CH$_2$Ph | H | bond | Li | 50 |
| OCH$_3$ | 2-OCH$_3$ | CH$_2$Ph | H | bond | Li | 62 |
| OCH$_3$ | 2-OCH$_3$ | H | H | bond | Li | 45 |
| OCH$_2$Ph | 2,3-(OCH$_2$Ph)$_2$ | CH$_2$Ph | H | bond | Li | 57 |
| OCH$_3$ | 2-OCH$_3$ | H | 2,6-(CH$_3$)$_2$ | bond | Li | 70 |
| OCH$_3$ | 2-OCH$_3$ | H | 2-CH$_3$ | bond | Li | 75 |
| OCH$_3$ | 2-OCH$_3$ | H | H | CH$_2$ | Li | 50 |
| OCH$_3$ | 2-OCH$_3$ | CH$_2$Ph | H | CH$_2$ | Li | ca. 90** |

EXAMPLE 5

Use of various solvents in the synthesis of 1-(2-methoxyphenyl)- 4-methylpiperazine.

The reaction described in Example 1 is performed in various solvents or solvent mixtures. Reaction temperature 70° C.; reaction time 120 min. The following results are obtained: Table D.

TABLE D

| solvent | yield (%) |
| --- | --- |
| methyl-t-butyl ether (MTBE) | 36 |
| toluene + MTBE 1:1 | 45 |
| DABCO | 55 |
| MTBE + N,N,N',N'-tetramethylethylene-diamine (TMEDA) 1:1 | 66 |
| THF + methylpiperazine (MP) 5:1 | 66 |
| THF | 66 |
| MP | 70 |
| TMEDA + MP 5:1 | 76 |
| TMEDA | 77 |
| TMEDA + MP 1:1 | 82 |

The same above reaction is carried out in a mixture of styrene and THF (1:1), under reflux for 20 hours; the desired product is obtained in a yield of 73%.

We claim:

1. Method for the preparation of a compound of the formula 2

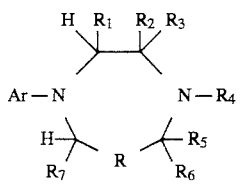 (2)

comprising reacting a compound of formula 3

Ar—Y    (3)

with a compound of the formula 4

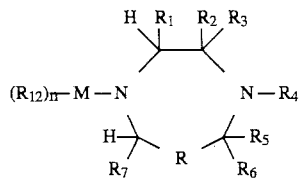 (4)

wherein

Ar means a (hetero)aryl group selected from the group consisting of phenyl, naphthyl, furyl, thienyl, pyridyl, and benzo-annelated and dibenzo-annelated heteroaryls, said heteroaryls being selected from the group consisting of furyl, thienyl and pyridyl, which (hetero)aryl group is unsubstituted or substituted with one to five non-strongly-electron-withdrawing substituents selected from the group consisting of deuterium; tritium; lower alkyl; lower alkenyl; lower alkoxy; lower alkylthio; phenylthio; hydroxyl halogen; trihalomethyl; di(lower)alkylamino, wherein the alkyl groups together with the amino-N may form a heterocyclic ring, which ring may contain a second heteroatom selected from N, O and S, and which ring may be substituted with lower alkyl; diphenylamino, unsubstituted phenyl, phenoxy and phenyl(lower)alkoxy; substituted phenyl, phenoxy and phenyl(lower)alkoxy, wherein the substituents are selected from the group consisting of halogen, lower alkyl, lower alkoxy, lower alkylthio, lower haloalkyl, hydroxy and di(lower)alkylamino; $(C_1-C_2)$alkylenedioxyl and $SO_2R_{11}$;

M means a metal from group I or II of the periodic table;

$R_{12}$ is an electronegative group selected from the group consisting of halogen, lower alkoxy, lower alkanoyloxy and a group of the formula 9

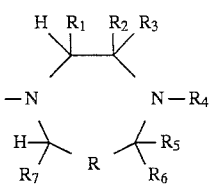 (9)

n is, dependent on the valence of M, 0 or 1;

R may be absent and represent a bond linking the two adjacent carbon atoms or means a group —$CR_8R_9$— or a carbonyl group;

$R_1$–$R_3$ and $R_5$–$R_9$ each mean mutually independently hydrogen, or lower alkyl or phenyl(lower)alkyl, wherein the alkyl groups may be substituted with halogen, lower alkoxy, hydroxy or protected hydroxy, and wherein the phenyl group may be substituted with halogen, lower alkyl, lower alkoxy, lower alkylthio, lower haloalkyl, hydroxy or di(lower)alkylamino;

$R_4$ means a hydrogen atom or a lower alkyl, aryl, aryl-(lower)alkyl, lower alkylsulphonyl, arylsulphonyl, lower trialkylsilyl, triarylsilyl, lower alkylcarbonyl, arylcarbonyl, lower alkyloxycarbonyl, or aryloxycarbonyl group, wherein aryl is phenyl or naphthyl; and Y means $OR_{10}$ chlorine, fluorine, or $SO_2R_{11}$, wherein
$R_{10}$ is lower alkyl, lower alkoxyalkyl, or phenyl or phenyl(lower)alkyl, wherein the phenyl group may be substituted with halogen, lower alkyl, lower alkoxy, lower alkylthio, lower haloalkyl, hydroxy or di(lower)alkylamino; and $R_{11}$ is hydroxy; OM, wherein M has the above meaning, lower alkyl; di(lower)alkylamino, wherein the alkyl groups together with the amino-N may form a heterocyclic ring, which ring may contain a second heteroatom selected from N, O and S, and which ring may be substituted with lower alkyl; diphenylamino; unsubstituted phenyl, phenoxy and phenyl(lower-)alkoxy; substituted phenyl, phenoxy and phenyl, (lower)alkoxy, wherein the substituents are selected from the group consisting of halogen, lower alkyl, lower alkoxy, lower alkylthio, lower haloalkyl, hydroxy and di(lower)alkylamino; diarylamino, wherein aryl is phenyl or naphthyl; or phenyl.

2. Method according to claim 1, wherein the reaction is carried out in a solvent which is neutral and inert with respect to the metallic reactant, or which solvent has the formula Ar—Y, defined in claim 1.

3. Method according to claim 2, wherein a member selected from the group consisting of a cyclic ether, an acyclic ether, a cyclic or acyclic tertiary amine, a hydrocarbon, and a mixture of these solvents is used as the solvent.

4. Method according to claim 1, wherein the reaction is performed at a temperature between room temperature and the reflux temperature of the solvent.

5. Method according to claim 2, wherein the reaction is performed at a temperature between room temperature and the reflux temperature of the solvent.

6. Method according to claim 3, wherein the reaction is performed at a temperature between room temperature and the reflux temperature of the solvent.

* * * * *